(12) United States Patent
Kim et al.

(10) Patent No.: US 8,927,763 B2
(45) Date of Patent: Jan. 6, 2015

(54) METHOD FOR PREPARING ALIPHATIC DIISOCYANATE

(71) Applicant: University-Industry Cooperation Group of Kyung Hee University, Yongin-si, Gyeonggi-do (KR)

(72) Inventors: Hoon Sik Kim, Seoul (KR); Heehwan Kim, Seoul (KR); Ji Young Oh, Seoul (KR); Seunghoon Shin, Seoul (KR); Seok Soo Kim, Gwacheon-si (KR); Kyung Sik Lim, Uijeongbu-si (KR); Jung Dae Choi, Incheon (KR)

(73) Assignee: University-Industry Cooperation Group of Kyung Hee University, Yongin-Si (KR)

( * ) Notice: Subject to any disclaimer, the term of this patent is extended or adjusted under 35 U.S.C. 154(b) by 0 days.

(21) Appl. No.: 14/365,427

(22) PCT Filed: Dec. 4, 2012

(86) PCT No.: PCT/KR2012/010424
§ 371 (c)(1),
(2) Date: Jun. 13, 2014

(87) PCT Pub. No.: WO2013/089381
PCT Pub. Date: Jun. 20, 2013

(65) Prior Publication Data
US 2014/0303399 A1    Oct. 9, 2014

(30) Foreign Application Priority Data

Dec. 14, 2011  (KR) ........................ 10-2011-0134861

(51) Int. Cl.
C07C 263/00    (2006.01)
C07C 265/14    (2006.01)
C07C 263/04    (2006.01)

(52) U.S. Cl.
CPC ............. *C07C 265/14* (2013.01); *C07C 263/04* (2013.01)
USPC .......................................................... 560/345

(58) Field of Classification Search
None
See application file for complete search history.

(56) References Cited

U.S. PATENT DOCUMENTS

| | | | |
|---|---|---|---|
| 3,919,279 A | | 11/1975 | Rosenthal et al. |
| 3,962,302 A | | 6/1976 | Rosenthal et al. |
| 4,294,774 A | * | 10/1981 | Henson et al. ................ 560/345 |
| 4,349,484 A | | 9/1982 | Merger et al. |
| 4,386,033 A | | 5/1983 | Konig et al. |
| 4,388,246 A | | 6/1983 | Sundermann et al. |
| 4,873,365 A | | 10/1989 | Luh et al. |

FOREIGN PATENT DOCUMENTS

| | | |
|---|---|---|
| DE | 1 022 222 A | 1/1958 |
| DE | 26 35 490 A1 | 2/1977 |
| KR | 10-0218656 B1 | 9/1999 |
| KR | 2010-0139076 A | 12/2010 |
| KR | 2011-0007184 A | 1/2011 |
| WO | 2011/067242 A1 | 6/2011 |

* cited by examiner

Primary Examiner — Karl J Puttlitz
(74) Attorney, Agent, or Firm — Sughrue Mion, PLLC

(57) ABSTRACT

The present invention relates to a method for preparing an aliphatic diisocyanate by pyrolyzing an aliphatic dicarbamate in liquid phase, using a tin (II) or (IV) compound as a catalyst and a zwitterionic compound as a stabilizer, thereby remarkably inhibiting high-boiling by-products and providing the aliphatic diisocyanate with high yield.

11 Claims, No Drawings

METHOD FOR PREPARING ALIPHATIC DIISOCYANATE

CROSS REFERENCE TO RELATED APPLICATIONS

This application is a National Stage of International Application No. PCT/KR2012/010424 filed Dec. 4, 2012, claiming priority based on Korean Patent Application No. 10-2011-0134861 filed Dec. 14, 2011, the contents of all of which are incorporated herein by reference in their entirety.

TECHNICAL FIELD

The present invention relates to a method for preparing an aliphatic diisocyanate. More particularly, the present invention relates to a method for preparing an aliphatic diisocyanate by pyrolyzing an aliphatic dicarbamate in liquid phase in the presence of a tin (II) or (IV) compound as a catalyst and a zwitterionic compound as a stabilizer, thereby remarkably inhibiting high-boiling by-products and providing the aliphatic diisocyanate with high yield.

BACKGROUND ART

Isocyanates, which are widely used as intermediates of polyurethane, adhesives, herbicides and pesticides, have been synthesized from amines and phosgene. However, since the method uses highly toxic phosgene, it has problems such as phosgene leak, equipment corrosion and the production of a lot of HCl causing pollution as a by-product. Therefore, there has been a need to develop a new eco-friendly method which does not use phosgene. Also, in view of the tendency that regulations on toxic substances are globally strengthened, research and development on green technology to synthesize isocyanates by non-phosgene process can be quite attractive in the chemical industry.

The isocyanates can be largely divided into aliphatic isocyanates and aromatic isocyanates, both of which are used as useful industrial raw materials. For example, polyurethane, which is prepared using aromatic 4,4-diphenylmethane diisocyanate (MDI) as a raw material, is widely used for microporous elastomer, thermoplastic elastomer, casting elastomer, artificial leather, synthetic leather, adhesive, coating, sealant, etc. Also, polyurethane form plastic, which is prepared using aromatic diisocyanates, 2,4- and 2,6-toluene diisocyanate (TDI), is used for elastomer milled with polyurethane elastomer, coating, adhesive, waterproof material, detergent, thickener, antioxidant, etc.

However, the polyurethane prepared from the aromatic diisocyanates has the problems of being yellowed by light after being exposed to the outside, thereby increasing the use of polyurethane prepared from non-yellowed aliphatic diisocyanates. For example, 1,6-hexane diisocyanate (HDI) is used for surface treatment paint and advanced coating for mainly car coating, surface treatment paint for anti-corrosion coating of airplanes, paint for enamel-insulated wire, paint for wood furniture, surface treatment paint for trains, polyurethane glue material having good light stability, rocket propellant additive, etc. In addition, 3-isocyanatomethyl-3,5,5-trimethylcyclohexylisocyanate(isophorone diisocyanate: IPDI) is widely used for aliphatic polyisocyanates such as polymers, trimers and adducts, waterproof polyurethane coating and various plastic products such as polyurethane leather, etc. Moreover, polyurethane prepared using 4,4-dicyclohexylmethane diisocyanate (HMDI) as a raw material is widely used for foam plastic, elastomer, coating, adhesive, anti-corrosion coating, paint for wood furniture, etc.

Among the eco-friendly methods to prepare isocyanates by non-phosgene process which have been known so far, the most economical and studied method is to prepare the isocyanates by reacting amines with dialkyl carbonate or urea/alcohol to synthesize carbamates, followed by pyrolyzing them. However, since a large amount of polymer by-products generated during the pyrolysis of the carbamates lower the isocyanate yields and block the flow of liquid to stop the equipment, various studies have been tried to solve the problems.

U.S. Pat. No. 3,962,302 discloses a method to synthesize TDI by pyrolyzing toluene diethylcarbamate, which flows nitrogen into the reactor in the presence of cetane solvent at 250° C. to obtain TDI with 83.4% yield. However, since the method uses nitrogen, it cannot be applied to practical process. U.S. Pat. No. 4,294,774 teaches a method to prepare MDI with 46% yield using N,N-dimethylaniline as a solvent and catalyst. Also, U.S. Pat. No. 4,349,484 discloses a method to prepare MDI with 76.5% yield by decomposing diphenylmethane dimethylurethane at 310° C. using zinc pieces as a catalyst in the presence of dicyclobenzene solvent. However, the above methods have the problems of low MDI yields, degradation and loss of the solvents due to vacuum and high temperature, and the generation of a large amount of high-boiling materials. In addition, DE Pat. No. 1,022,222, U.S. Pat. No. 3,919,279, DE Pat. No. 2,635,490, U.S. Pat. Nos. 4,873,365 and 4,386,033 disclose methods to prepare IPDI, HMDI or HDI by decomposing dicarbamates in the presence of a basic, acidic or organic metal compound catalyst and a suitable solvent, but they cannot avoid the formation of high-boiling by-products.

To reduce the formation of the high-boiling by-products, U.S. Pat. No. 4,388,246 discloses a method to prepare diisocyanates by pyrolyzing dicarbamates using hydrogen chloride, chlorinated organic acid, alkyl ester having alkylation function, or inorganic acid salt of alkyl ester as a stabilizer and organic tin chloride compound as a catalyst. Despite using the catalyst and stabilizer, the formation of the high-boiling by-products was not significantly reduced, and the diisocyanate yields were not high enough.

For these reasons, methods which use heavy metal such as Co, Mn, Fe and Ni, or metal compounds thereof as a catalyst were proposed, but they also had the problems that high-boiling by-products were accumulated in the reactor since high-boiling by-products were generated, thereby reducing the catalyst activity.

DISCLOSURE

Technical Problem

The present inventors have endeavored to overcome the above problems and found that the yield of the aliphatic diisocyanate can be increased and the formation of the high-boiling by-products can be remarkably reduced by pyrolyzing an aliphatic dicarbamate in liquid phase, using a tin (II) or (IV) compound as a catalyst and a zwitterionic compound as a stabilizer.

An object of the present invention is, therefore, to provide a method for eco-friendly preparing an aliphatic diisocyanate with high yield while reducing the formation of the high-boiling by-products.

Technical Solution

One aspect of the present invention relates to a method for preparing an aliphatic diisocyanate by pyrolyzing a $C_4$-$C_{12}$ aliphatic dicarbamate in liquid phase, which uses a tin (II) or (IV) compound as a catalyst and one or more zwitterionic compounds of the following formula (1) to (5) as a stabilizer:

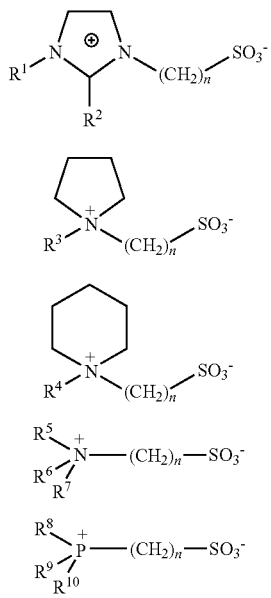

wherein, $R^1$, $R^5$, $R^6$, $R^7$, $R^8$, $R^9$ and $R^{10}$ are each independently $C_1$-$C_6$ alkyl or aryl;

$R_2$ is H or methyl;

$R_3$ and $R_4$ are each independently $C_1$-$C_4$ alkyl; and n is 3 or 4.

The term "alkyl" as used herein means a straight or branched hydrocarbon, which includes methyl, ethyl, propyl, butyl, etc., but is not limited thereto.

The term "aryl" as used herein includes all of aromatic group, heteroaromatic group and partially reduced derivatives thereof. The aromatic group means a 5 to 15-membered simple or fused ring. The heteroaromatic group means an aromatic group containing at least one atom selected from oxygen, sulfur and nitrogen. Examples of the aryl include phenyl, benzyl, naphthyl, pyridinyl, furanyl, thiophenyl, indolyl, quinolinyl, imidazolinyl, oxazolyl, thiazolyl, tetrahydronaphthyl, etc., but are not limited thereto.

The $C_4$-$C_{12}$ aliphatic dicarbamate used in the method of the present invention includes a $C_4$-$C_{12}$ cycloaliphatic dicarbamate. Examples of the $C_4$-$C_{12}$ aliphatic dicarbamate include 1,2-bis(methoxycarbonylamino)ethane, 1,3-bis(methoxycarbonylamino)propane, 1,4-bis(methoxycarbonylamino)butane, 1,6-bis(methoxycarbonylamino)hexane, 1,6-bis(ethoxycarbonylamino)hexane, 1,6-bis(butoxycarbonylamino)hexane, 1,8-bis(methoxycarbonylamino)octane, 1,8-bis(butoxycarbonylamino)octane, 1,2-bis(methoxycarbonylamino)cyclohexane, 1,2-bis(butoxycarbonylamino)cyclohexane, 1,3-bis(methoxycarbonylamino)cyclohexane, 1,3-bis(butoxycarbonylamino)cyclohexane, 1,4-bis(methoxycarbonylamino)cyclohexane, 1,4-bis(butoxycarbonylamino)cyclohexane, 1,2-bis(methoxycarbonylaminomethyl)cyclohexane, 1,2-bis(butoxycarbonylaminomethyl)cyclohexane, 1,3-bis(methoxycarbonylaminomethyl)cyclohexane, 1,3-bis(butoxycarbonylaminomethyl)cyclohexane 1,4-bis(methoxycarbonylaminomethyl)cyclohexane, 1,4-bis(butoxycarbonylaminomethyl)cyclohexane, 4.4-methylenedi(methoxycarbonylaminocyclohexane), 4.4-methylenedi(butoxycarbonylaminocyclohexane), bis(methoxycarbonyl) isophorone, bis(butoxycarbonyl) isophorone, etc., but are not limited thereto.

The tin (II) or (IV) compound used in the method of the present invention includes bis(tri-n-butyltin)oxide, bis(tri-n-butyltin) sulfate, di-n-butyldiphenyltin, di-n-butyltin bis(acetylacetonate), di-n-butyltin bis(2-ethylhaxanoate), di-n-butyltin dichloride, di-n-butyltin dilaurate, di-n-butyltinoxide, dimethyldiphenyltin, dimethyltin dichloride, diphenyltin dichloride, diphenyltinoxide, hexa-n-butyltin, hexaphenyltin, tetra-n-butyltin, tetraphenyltin, tin (II) acetate, tin (II) acetylacetonate, tin (II) chloride, tin (II) iodide, tin (II) oxalate, etc., but are not limited thereto.

The tin compound catalyst may be used in an amount of 0.01 to 5 wt %, preferably 0.02 to 3 wt %, more preferably 0.05 to 1 wt %, based on the aliphatic dicarbamate. If the amount of the catalyst is less than 0.01 wt %, the reaction rate can be lowered. If the amount of the catalyst is more than 5 wt %, the reaction rate and yield cannot be improved any more, thereby providing no more economic benefits.

The zwitterionic compound is used in an amount of 0.05 to 10 wt %, preferably 0.1 to 5 wt %, based on the aliphatic dicarbamate. If the amount of the zwitterionic compound is less than 0.05 wt %, the effect of inhibiting the formation of the high-boiling compounds can be minimal. If the amount of the zwitterionic compound is more than 10 wt %, the zwitterionic compound can be used more than necessary, thereby increasing the amount of the zwitterionic compound to be recovered after the reaction.

The pylosis reaction can be conducted in the presence of a reaction solvent. Specifically, a high-boiling solvent which is inert to the aliphatic dicarbamate and the aliphatic diisocyanate product can be used. The high-boiling solvent includes hydrocarbons such as dodecane and hexadecane; aromatic hydrocarbons such as biphenyl, terphenyl, benzyltoluene, triphenylmethane, phenylnaphthalene and benzylnaphthalene; esters such as dioctyl phthalate and didecyl phthalate; diphenyl sulfone; ethers such as diphenyl ether and dibenzyl ether, etc., but are not limited thereto.

The reaction solvent is used in an amount of 0.5 to 20 times, preferably 2 to 10 times the weight of the aliphatic dicarbamate. If the amount of the solvent is less than 0.5 times, the viscosity can be high and the stirring or the flow of liquid cannot be smooth, thereby increasing the generation of the high-boiling by-products. If the amount of the solvent is more than 10 times, the solvent can be used more than necessary, thereby increasing the amount of the solvent to be recovered after the reaction and increasing energy consumption.

The pyrolysis reation temperature can be 180to 300° C. preferably 220 to 270° C. If the reaction temperature is less than 180° C. the pyrolysis rate can be slow, thereby lowering the yield of the diisocyanate. If the reaction temperature is more than 300° C. the formation of the high-boiling by-products can be significantly increased.

The pyrolysis reaction is preferably conducted under reduced pressure, and the reaction pressure can be 0.1 to 100 mmHg, preferably 1 to 50 mmHg. If the reaction pressure is less than 0.1 mmHg, the high-boiling solvent can be vaporized to come out of the reactor together with the diisocyanate product. If the reaction pressure is more than 100 mmHg, the diisocyanate can be stayed in the reactor for a long time to be polymerized.

The residence time of the reactants in the reactor can vary depending on the reactants, the amount of the catalyst, the reaction temperature, the reaction pressure, the reactor type, etc., but it is preferably 0.1 to 5 hours.

In the method of the present invention, the aliphatic dicarbamate is decomposed by heat into the diisocyanate and alcohol. However, since the decomposed diisocyanate and alcohol can react to return to the original dicarbamate, it is important to separately collect the decomposed diisocyanate and alcohol.

The pyrolysis reaction can be conducted by a batch or continuous process, but the continous process is more effective for inhibiting the high-boiling compounds. The batch process is to fill a reactor equipped with a reflux apparatus and cooler with the reactants consisting of the dicarbamate, high-boiling solvent, catalyst and zwitterionic compound, which are subject to pyrolysis at a given temperature and pressure for a given time, and collect the resulting diisocyanate and alcohol. The continuous process is to continuously supply a reactor with the reactants consisting of the dicarbamate, high-boiling solvent, catalyst and zwitterionic compound while pyrolyzing the reactants under reduced pressure, and distill the products coming out of the reactor to separate and recover the diisocyanate and alcohol.

Advantageous Effects

In accordance with the present invention, the aliphatic diisocyanate can be prepared by pyrolyzing the aliphatic dicarbamate in liquid phase, using a tin (II) or (IV) compound as a catalyst and a zwitterionic compound as a stabilizer, thereby remarkably inhibiting high-boiling by-products and providing the aliphatic diisocyanate with high yield.

BEST MODE

The present invention is further illustrated by the following examples, which are not to be construed to limit the scope of the invention.

EXAMPLE 1

500 mL 3-necked flask equipped with a reflux apparatus, cooler, thermometer and sampling device was charged with 1,6-bis(methoxycarbonylamino)hexane (HDC, 50 g), benzyltoluene (250 g), di-n-butyltin dilaurate (0.05 g), and 1-methylimidazolium-3-propanesulfonate (0.1 g) as a zwitterionic compound, which were heated to 240° C. under 20 mmHg pressure. The reaction time was 2 hours, and the temperature of the reflux and cooling condenser was kept at 60° C. or more to prevent the reverse reaction. The resulting 1,6-diisocyanatohexane (HDI) and methanol were separately collected into a flask and dry ice-acetone trap. After the completion of the reaction, the product collected in the flask was analyzed with gas chromatography, which showed 94.1% yield of HDI, 5.2% yield of 1-isocyanato-6-methoxycarbonylaminohexane (HMI), and only 1.3 g of high-boiling polymer precipitates.

COMPARATIVE EXAMPLE 1

The pyrolysis reaction of the HDC was conducted in accordance with the process described in Example 1, without using 1-methylimidazolium-3-propanesulfonate as a stabilizer. As a result, the yield of HDI and HMI and the amount of the high-boiling polymer precipitates was 71.4%, 7.3% and 8.2 g, respectively.

EXAMPLE 2 to 7

The pyrolysis reaction was conducted in accordance with the process described in Example 1, with changing wt % of the catalyst to HDC. The results were shown in Table 1.

TABLE 1

| Example | Catalyst/HDC (wt %) | Yield (%) HDI | HMI | Polymer (g) |
|---|---|---|---|---|
| 2 | 0.01 | 88.5 | 6.7 | 1.7 |
| 3 | 0.03 | 89.3 | 5.5 | 1.4 |
| 4 | 0.2 | 95.2 | 3.1 | 1.2 |
| 5 | 0.5 | 95.4 | 2.8 | 1.2 |
| 6 | 1 | 96.3 | 2.1 | 1.1 |
| 7 | 5 | 97.4 | 1.6 | 0.9 |

EXAMPLE 8 to 13

The pyrolysis reaction was conducted in accordance with the process described in Example 1, with changing wt % of the zwitterionic compound stabilizer (1-methylimidazolium-3-propanesulfonat) to HDC. The results were shown in Table 2.

TABLE 2

| Example | Stabilizer/HDC (wt %) | Yield (%) HDI | HMI | Polymer (g) |
|---|---|---|---|---|
| 8 | 0.05 | 86.4 | 5.3 | 3.7 |
| 9 | 0.1 | 87.3 | 4.7 | 2.4 |
| 10 | 0.5 | 94.7 | 4.1 | 1.1 |
| 11 | 1.0 | 94.9 | 3.8 | 0.7 |
| 12 | 5 | 95.1 | 3.2 | 0.4 |
| 13 | 10 | 95.9 | 2.8 | 0.2 |

EXAMPLE 14 to 24

The pyrolysis reaction was conducted in accordance with the process described in Example 1, with changing the stabilizer. The results were shown in Table 3.

TABLE 3

| Example | Stabilizer | Yield (%) HDI | HMI | Polymer (g) |
|---|---|---|---|---|
| 14 | 1-butylimidazolium-3-propanesulfonate | 92.9 | 5.2 | 1.5 |
| 15 | 1-phenylimidazolium-3-propanesulfonate | 92.4 | 5.7 | 1.7 |
| 16 | 1-methylimidazolium-3-butanesulfonate | 94.3 | 4.9 | 1.6 |
| 17 | tributylammonium propanesulfonate | 93.1 | 5.5 | 1.5 |
| 18 | trihexylammonium butanesulfonate | 92.5 | 5.7 | 1.7 |
| 19 | triphenylphosphonium propanesulfonate | 95.1 | 4.3 | 1.6 |
| 20 | diphenylmethylphosphonium butanesulfonate | 96.2 | 3.3 | 1.2 |
| 21 | 1-methylpyrrolidinium-3-propanesulfonate | 92.7 | 6.1 | 1.1 |
| 22 | 1-butylpyrrolidinium-3-butanesulfonate | 91.5 | 6.5 | 1.6 |
| 23 | 1-methylpiperidinium-3-propanesulfonate | 90.8 | 6.9 | 1.5 |

TABLE 3-continued

| Example | Stabilizer | Yield (%) HDI | Yield (%) HMI | Polymer (g) |
|---|---|---|---|---|
| 24 | 1-hexylpiperidinium-3-butanesulfonate | 89.9 | 7.3 | 1.7 |

EXAMPLE 25 to 30

The pyrolysis reaction was conducted in accordance with the process described in Example 1, with changing the weight ratio of the solvent (benzyltoluene) to HDC. The results were shown in Table 4.

TABLE 4

| Example | Solvent/HDC (weight ratio) | Yield (%) HDI | Yield (%) HMI | Polymer (g) |
|---|---|---|---|---|
| 25 | 0.5 | 82.4 | 7.3 | 3.9 |
| 26 | 1 | 84.3 | 6.7 | 2.9 |
| 27 | 3 | 91.8 | 5.2 | 2.4 |
| 28 | 7 | 95.9 | 3.4 | 0.8 |
| 29 | 10 | 96.4 | 3.1 | 0.5 |
| 30 | 20 | 97.2 | 2.6 | 0.1 |

EXAMPLE 31 to 37

The pyrolysis reaction was conducted in accordance with the process described in Example 1, with changing the pyrolysis temperature and pressure. The results were shown in Table 5.

TABLE 5

| Example | Temperature (° C.) | Pressure (mmHg) | Yield (%) HDI | Yield (%) HMI | Polymer (g) |
|---|---|---|---|---|---|
| 31 | 180 | 0.1 | 63.2 | 8.7 | 0.1 |
| 32 | 200 | 10 | 71.3 | 7.5 | 0.3 |
| 33 | 220 | 20 | 82.5 | 6.3 | 0.7 |
| 34 | 240 | 10 | 95.6 | 3.5 | 1.1 |
| 35 | 250 | 30 | 92.7 | 2.1 | 2.3 |
| 36 | 270 | 50 | 89.3 | 1.5 | 3.7 |
| 37 | 300 | 100 | 78.5 | 0.7 | 7.9 |

EXAMPLE 38 to 47

The pyrolysis reaction was conducted in accordance with the process described in Example 1, with changing the catalyst. The results were shown in Table 6.

TABLE 6

| Example | Catalyst | Yield (%) HDI | Yield (%) HMI | Polymer (g) |
|---|---|---|---|---|
| 38 | bis(tri-n-butyltin)oxide | 92.7 | 5.8 | 1.7 |
| 39 | bis(tri-n-butyl) sulfate | 91.5 | 5.9 | 1.8 |
| 40 | di-n-butyltin dichloride | 92.3 | 5.2 | 1.5 |
| 41 | diphenyltin dichloride | 90.7 | 4.4 | 1.6 |
| 42 | tin(II) oxalate | 90.2 | 4.7 | 1.9 |
| 43 | diphenyltinoxide | 91.1 | 5.0 | 1.3 |
| 44 | tin(II) acetylacetonate | 89.3 | 4.9 | 2.1 |
| 45 | tetra-n-butyltin | 83.8 | 7.1 | 2.4 |

TABLE 6-continued

| Example | Catalyst | Yield (%) HDI | Yield (%) HMI | Polymer (g) |
|---|---|---|---|---|
| 46 | hexaphenyltin | 84.2 | 7.5 | 2.3 |
| 47 | tetraphenyltin | 79.3 | 8.1 | 2.2 |

EXAMPLE 48 to 57

The pyrolysis reaction was conducted in accordance with the process described in Example 1, with changing the solvent. The results were shown in Table 7.

TABLE 7

| Example | Solvent | Yield (%) HDI | Yield (%) HMI | Polymer (g) |
|---|---|---|---|---|
| 48 | dodecane | 88.9 | 7.2 | 2.4 |
| 49 | hexadecane | 89.2 | 5.3 | 2.2 |
| 50 | biphenyl | 91.2 | 4.8 | 2.1 |
| 51 | terphenyl | 95.1 | 3.7 | 1.2 |
| 52 | phenylnaphthalene | 95.2 | 3.3 | 1.2 |
| 53 | triphenylmethane | 91.4 | 3.2 | 1.1 |
| 54 | benzylnaphthalene | 93.1 | 3.3 | 1.2 |
| 55 | didecyl phthalate | 89.9 | 5.9 | 3.1 |
| 56 | dibenzyl ether | 94.2 | 2.8 | 1.5 |
| 57 | diphenyl sulfone | 91.2 | 4.6 | 1.7 |

EXAMPLE 58 to 66

The pyrolysis reaction was conducted in accordance with the process described in Example 1, with changing the dicarbamate. The results were shown in Table 8.

TABLE 8

| Example | Dicarbamate | Diisocyanate Yield (%) | Polymer (g) |
|---|---|---|---|
| 58 | 1,2-bis(methoxycarbonyl-amino)ethane | 96.1 | 1.2 |
| 59 | 1,4-bis(methoxycarbonyl-amino)butane | 95.2 | 1.2 |
| 60 | 1,2-bis(butoxycarbonyl-amino)cyclohexane | 95.3 | 1.3 |
| 61 | 1,3-bis(methoxycarbonylaminomethyl)cyclohexane | 94.9 | 1.1 |
| 62 | 1,4-bis(butoxycarbonylamino-methyl)cyclohexane | 94.8 | 1.0 |
| 63 | bis(butoxycarbonyl)isophorone | 93.9 | 0.8 |
| 64 | bis(methoxycarbonyl)isophorone | 94.4 | 1.1 |
| 65 | 4,4-methylenedi(methoxycarbonyl-aminocyclohexane) | 95.7 | 0.9 |
| 66 | 4,4-methylenedi(butoxycarbonyl-aminocyclohexane) | 95.4 | 1.1 |

The invention claimed is:

1. A method for preparing an aliphatic diisocyanate by pyrolyzing a $C_4$-$C_{12}$ aliphatic dicarbamate in liquid phase, which uses a tin (II) or (IV) compound as a catalyst and one or more zwitterionic compounds of the following formula (1) to (5) as a stabilizer:

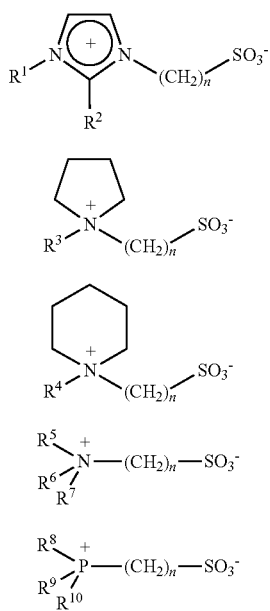

wherein, $R^1$, $R^5$, $R^6$, $R^7$, $R^8$, $R^9$ and $R^{10}$ are each independently $C_1$-$C_6$ alkyl or aryl;

$R_2$ is H or methyl;

$R_3$ and $R_4$ are each independently $C_1$-$C_4$ alkyl; and n is 3 or 4.

2. The method according to claim 1, wherein the aliphatic dicarbamate is 1,2-bis(methoxycarbonylamino)ethane, 1,3-bis(methoxycarbonylamino)propane, 1,4-bis(methoxycarbonylamino)butane, 1,6-bis(methoxycarbonylamino)hexane, 1,6-bis(ethoxycarbonylamino)hexane, 1,6-bis(butoxycarbonylamino)hexane, 1,8-bis(methoxycarbonylamino)octane, 1,8-bis(butoxycarbonylamino)octane, 1,2-bis(methoxycarbonylamino)cyclohexane, 1,2-bis(butoxycarbonylamino)cyclohexane, 1,3-bis(methoxycarbonylamino)cyclohexane, 1,3-bis(butoxycarbonylamino)cyclohexane, 1,4-bis(methoxycarbonylamino)cyclohexane, 1,4-bis(butoxycarbonylamino)cyclohexane, 1,2-bis(methoxycarbonylaminomethyl)cyclohexane, 1,2-bis(butoxycarbonylaminomethyl)cyclohexane, 1,3-bis(methoxycarbonylaminomethyl)cyclohexane, 1,3-bis(butoxycarbonylaminomethyl)cyclohexane, 1,4-bis(methoxycarbonylaminomethyl)cyclohexane, 1,4-bis(butoxycarbonylaminomethyl)cyclohexane, 4.4-methylenedi(methoxycarbonylaminocyclohexane), 4.4-methylenedi(butoxycarbonylaminocyclohexane), bis(methoxycarbonyl) isophorone, or bis(butoxycarbonyl) isophorone.

3. The method according to claim 1, wherein the tin (II) or (IV) compound is bis(tri-n-butyltin)oxide, bis(tri-n-butyltin) sulfate, di-n-butyldiphenyltin, di-n-butyltin bis(acetylacetonate), di-n-butyltin bis(2-ethylhaxanoate), di-n-butyltin dichloride, di-n-butyltin dilaurate, di-n-butyltinoxide, dimethyldiphenyltin, dimethyltin dichloride, diphenyltin dichloride, diphenyltinoxide, hexa-n-butyltin, hexaphenyltin, tetra-n-butyltin, tetraphenyltin, tin (II) acetate, tin (II) acetylacetonate, tin (II) chloride, tin (II) iodide, or tin (II) oxalate.

4. The method according to claim 1, wherein the catalyst is used in an amount of 0.01 to 5 wt % based on the aliphatic dicarbamate.

5. The method according to claim 1, wherein the zwitterionic compound is used in an amount of 0.05 to 10 wt % based on the aliphatic dicarbamate.

6. The method according to claim 1, wherein the reaction temperature is 180 to 300° C.

7. The method according to claim 1, wherein the reaction pressure is 0.1 to 100 mmHg.

8. The method according to claim 1, wherein the pyrolysis reaction is conducted by a continuous process.

9. The method according to claim 1, wherein the pyrolysis reaction is conducted in the presence of a reaction solvent.

10. The method according to claim 9, wherein the reaction solvent is one or more high-boiling solvents selected from the group consisting of dodecane, hexadecane, biphenyl, terphenyl, benzyltoluene, triphenylmethane, phenylnaphthalene, benzylnaphthalene, dioctyl phthalate, didecyl phthalate, diphenyl sulfone, diphenyl ether and dibenzyl ether.

11. The method according to claim 9, wherein the reaction solvent is used in an amount of 0.5 to 20 times the weight of the aliphatic dicarbamate.

\* \* \* \* \*